United States Patent
Cook et al.

(10) Patent No.: US 10,420,500 B2
(45) Date of Patent: Sep. 24, 2019

(54) IMAGING DEVICE FOR MEASURING CHARACTERISTICS OF A HAIR OR A SCALP

(71) Applicant: Conopco, Inc., Englewood Cliffs, NJ (US)

(72) Inventors: Joanne Louise Cook, Wirral (GB); Myriam Fessi, Liverpool (GB); Mark Robert Florence, Newton, MA (US); Abid Iftikhar, Liverpool (GB); Jamie Gordon Nichol, Carlisle, MA (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/754,437

(22) PCT Filed: Aug. 16, 2016

(86) PCT No.: PCT/EP2016/069367
§ 371 (c)(1),
(2) Date: Feb. 22, 2018

(87) PCT Pub. No.: WO2017/032636
PCT Pub. Date: Mar. 2, 2017

(65) Prior Publication Data
US 2018/0235535 A1    Aug. 23, 2018

(30) Foreign Application Priority Data
Aug. 27, 2015 (EP) ................................. 15182759

(51) Int. Cl.
*A61B 5/00* (2006.01)
*G02B 21/00* (2006.01)
*G02B 21/36* (2006.01)

(52) U.S. Cl.
CPC .............. *A61B 5/448* (2013.01); *A61B 5/446* (2013.01); *G02B 21/0008* (2013.01); *G02B 21/36* (2013.01); *A61B 5/0013* (2013.01)

(58) Field of Classification Search
CPC combination set(s) only.
See application file for complete search history.

(56) References Cited

U.S. PATENT DOCUMENTS

2003/0012461 A1* 1/2003 Satoh ................... A61B 5/0059
382/325
2003/0078971 A1   4/2003 Mori et al.
(Continued)

FOREIGN PATENT DOCUMENTS

JP    2001324680    11/2001
JP    2014113467    6/2014
(Continued)

OTHER PUBLICATIONS

IPRP1 in PCTEP2016069367, Feb. 27, 2018.
(Continued)

*Primary Examiner* — Janese Duley
(74) *Attorney, Agent, or Firm* — Foley & Lardner LLP

(57) ABSTRACT

A hand held imaging device for measuring characteristics of hair and scalp, comprising a housing with a high magnification optic for obtaining magnified images of surface characteristics of hair fibers, said high magnification optic comprising a first lens and a first light source, and a low magnification optic for obtaining magnified images of the scalp and hair, said low magnification optic comprising a second lens and a second light source, wherein the high magnification optic has a fixed focal length and a slot for locating hair fibers in frame such that the hair fibers are in focus and wherein the device further comprises a viewing means, selected from an integral viewing means, an external viewing means and a combination thereof.

15 Claims, 4 Drawing Sheets

(56) References Cited

U.S. PATENT DOCUMENTS

| | | | |
|---|---|---|---|
| 2003/0227612 A1* | 12/2003 | Fein | G02B 21/365 356/39 |
| 2006/0005409 A1* | 1/2006 | Cohen | A61B 5/1072 33/512 |
| 2006/0085274 A1 | 4/2006 | Sottery et al. | |
| 2008/0194928 A1* | 8/2008 | Bandic | G16H 15/00 600/306 |
| 2011/0090328 A1* | 4/2011 | Chen | G02B 21/0008 348/79 |
| 2012/0041284 A1* | 2/2012 | Krishnan | A61B 5/0075 600/306 |
| 2012/0120223 A1 | 5/2012 | Zuest et al. | |

FOREIGN PATENT DOCUMENTS

| | | |
|---|---|---|
| WO | WO2010049907 | 5/2010 |
| WO | WO2013160793 | 10/2013 |
| WO | WO2014040853 | 3/2014 |

OTHER PUBLICATIONS

IPRP2 in PCTEP2016069368, Nov. 29, 2017.
Search Report and Written Opinion in EP15182759, dated Feb. 10, 2016.
Search Report and Written Opinion in PCTEP2016069367, dated Oct. 10, 2016.
Search Report and Written Opinion in PCTEP2016069368, dated Oct. 28, 2016.
Search Report in EP15182780, dated Oct. 15, 2015.
Written Opinion in EP15182780, dated Oct. 15, 2015.
Written Opinion2 in PCTEP2016069368, dated Jul. 28, 2017.
Co-Pending U.S. Appl. No. 15/754,447, filed Feb. 22, 2018.

* cited by examiner

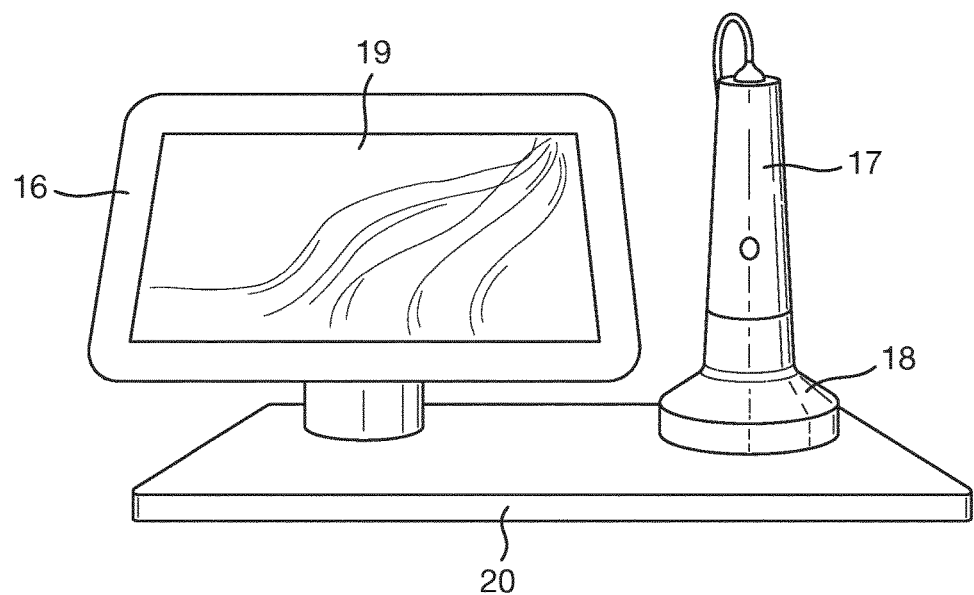

IMAGING DEVICE FOR MEASURING CHARACTERISTICS OF A HAIR OR A SCALP

CROSS-REFERENCE TO RELATED APPLICATIONS

This Application claims priority to International Patent Application No. PCT/EP2016/069367, filed on Aug. 16, 2016, and European Patent Application No. 15182759.9, filed on Aug. 27, 2015, both of which are incorporated herein by reference in their entireties.

TECHNICAL FIELD OF THE INVENTION

The present disclosure relates to a microscope type device for evaluating the condition of hair and scalp and recommending suitable products/solution/regime for the consumer and a method of evaluating and recommending products, using the device.

BACKGROUND

It is useful to evaluate properties of hair. Particularly useful assessments include visual damage along the hair fibre, for example, split ends at the hair tips; cuticle condition; hair diameter (which can be indicative of a number of attributes linked with healthy or damaged hair); scalp sebum; scalp dandruff; hair abundance (how many hairs in a specific area of scalp) and follicle occupancy (number of hairs coming out of each follicle). Evaluation of such properties enables the beneficial choice of products that suit the particular condition of the hair.

These properties are linked to a number of consumer hair concerns for scalp and hair condition and impact consumers' choice of hair care products. Selection of appropriate products for any given individual often begins with an evaluation of the individual's scalp and/or hair.

Although consumers do self-assess their scalp and hair condition, such qualitative self-assessments frequently lack accuracy. Further, such assessments do not comprise a benchmarking step against a reference standard for good and bad condition.

There are a number of microscopes available for such assessments.

US2012/0120223 discloses a portable microscope comprising an integrated operator control unit configured for at least one of selecting and adjusting at least one electrically controllable function of the microscope. The operator control unit includes at least one sensor configured to receive user control commands for at least one of activation, deactivation and adjustment thereof. The sensor includes a touch sensor and is disposed so as to accommodate holding and operation of the microscope with a single hand of the user.

Our co-pending application, WO2014/040853 discloses a device for evaluating skin and/or hair condition which device comprises: a) a housing; b) a hydration meter for measuring moisture or hydration value, which meter is supported by and projects from at least one end of the housing, the end of which meter comprises a surface evaluation area having an aspect ratio wherein the width is greater than length or width is greater than height (>1:1 to about 20:1); c) a camera supported by and projecting from a separate end of said housing; and d) a further separate end comprising an electrical wire or cord terminating in a means for communicating with a computer.

However, these devices lack the functionality relating to the optimization of resolution and polarity from a single unit device. Most of the high resolution microscopes on the market require extra effort to obtain a high resolution focused image and hence require trained personnel to carry out such procedures. There is a need to address these issues.

We have now found that hair and scalp can be conveniently and effectively examined using a hand held imaging device comprising both a high and a low magnification optic, wherein the high magnification optic has a slot for locating hair fibres in frame, and a fixed focal length configured such that the located hair fibres are in focus and no manual focusing is required.

SUMMARY

In a first aspect of the present disclosure, there is provided a hand held imaging device for measuring characteristics of hair and scalp, comprising a housing with a high magnification optic for obtaining magnified images of surface characteristics of hair fibres, said high magnification optic comprising a first lens and a first light source, and a low magnification optic for obtaining magnified images of the scalp and hair, said low magnification optic comprising a second lens and a second light source, wherein the high magnification optic has a fixed focal length and a slot for locating hair fibres in frame such that the hair fibres are in focus and wherein the device further comprises a viewing means, selected from an integral viewing means, an external viewing means and a combination thereof.

In a second aspect there is provided a method for evaluating condition of hair and scalp using the imaging device of the first aspect, and recommending products appropriate to the condition of the hair, which method comprises the steps of:—
1) placing hair fibres in the slot and obtaining a high resolution image of the fibres;
2) optionally placing the low magnification optic onto the hair or scalp and obtaining an image;
3) using the images of steps 1) and 2) to make an assessment of the condition of the hair or scalp; and
4) using the assessment of step 3) to provide a product recommendation.

In a third aspect, the present disclosure provides a workstation comprising the hand held imaging device of the first aspect and a screen, wherein the hand held device and the screen are positioned on a unitary base.

It will be clear to the skilled person that the hand held imaging device of the present may be used for measuring characteristics of many different types of fibres, for example, hair, wool, textiles, synthetic fibres by using the slot (4) of the high magnification optic.

BRIEF DESCRIPTION OF THE FIGURES

Embodiments of the present disclosure will now be described with reference to the following non-limiting drawings in which:

FIG. 5 is a perspective view of a workstation (16) comprising the hand held imaging device.

FIG. 1 is a perspective view of the device comprising a housing (1), a high magnification optic (2), a low magnification optic (3), a slot (4), a means for connecting to an external viewing means (5), a shutter button (6), a gripping portion (7) and a spacer cap (8).

FIG. 2 is a view of the device showing internal elements. In this figure, the high magnification optic (2) is shown along with its component first lens (9) and first light source (10), and the low magnification optic (3) is also shown to comprise a second lens (11) and a second light source (12).

FIG. 3 is a perspective view of the slot feature in use. A bundle of hair fibres (13) is held in the slot (4) to obtain a high resolution image.

FIG. 4 is a view of the low magnification end showing the supporting ring (15) with eight spatially arranged lights (14). The spacer cap (8) can be twisted in order to polarize the light.

FIG. 5 is a perspective view of a workstation (16) comprising the hand held imaging device (17) resting in a stand (18) and a screen (19), all positioned on a unitary base (20).

DETAILED DESCRIPTION

Figure 1:
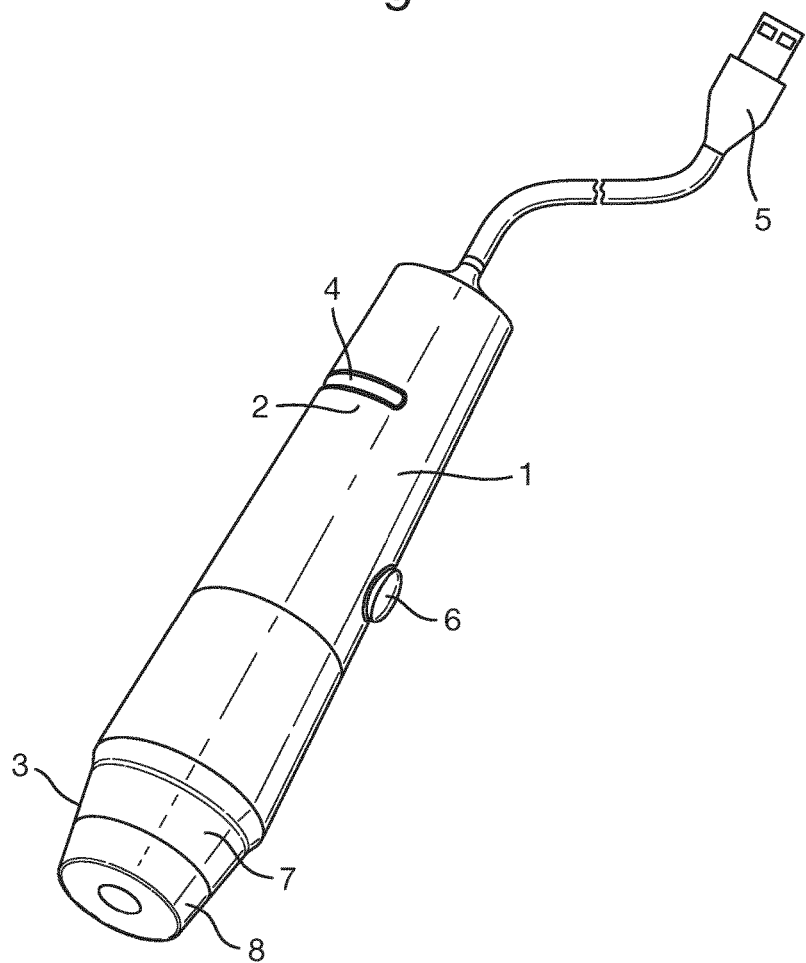
FIG. 1 is a perspective view of a hand held imaging device in accordance with the present disclosure.
Figure 2:
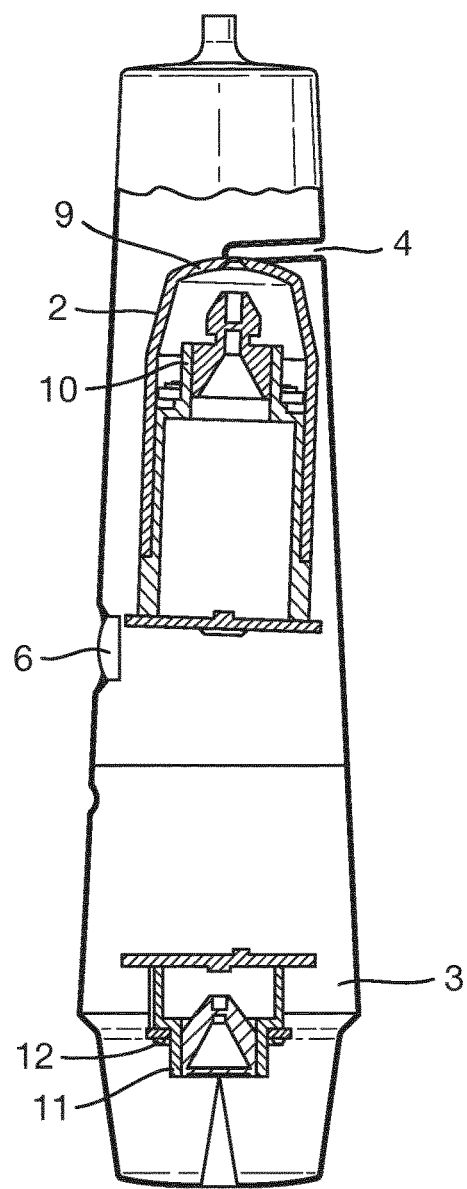
FIG. 2 is a perspective view of a hand held imaging device showing internal elements.
Figure 3:
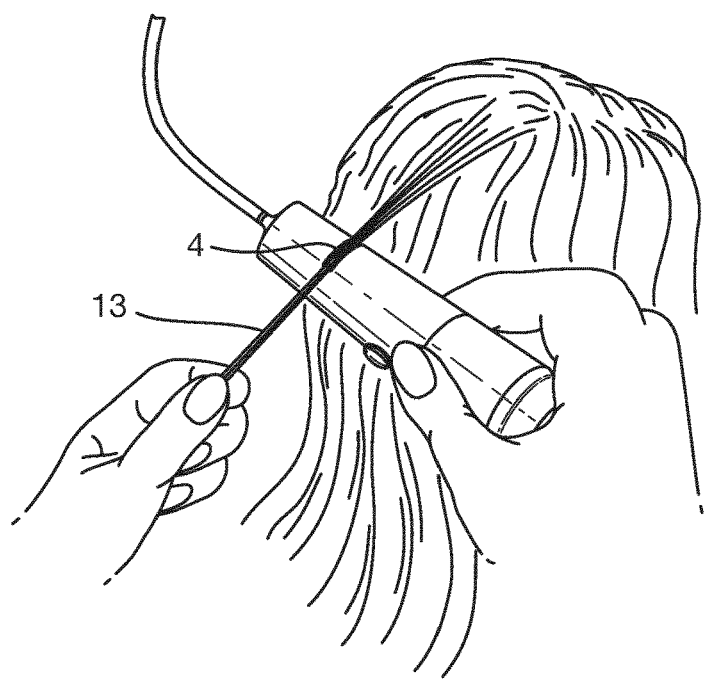
FIG. 3 is a perspective view of a hand held imaging device in use.
Figure 4:
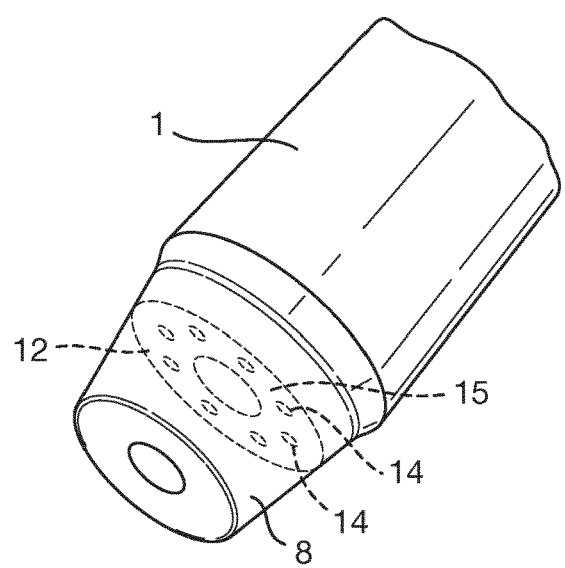
FIG. 4 is a view of the low magnification end showing the supporting ring (15) with eight spatially arranged lights.

The present disclosure relates to a hand held imaging device for measuring characteristics of hair and scalp.

By the terms "hand-holdable" or "hand held" is meant a device typically measuring in length (not including any cord) less than 35 centimeters (cm), preferably between 10 and 25 cm and a width between 2 and 8 cm, preferably between 3 and 6 cm.

The device is preferably a microscope.

The device preferably has a tip end that can be held in close proximity to the scalp and roots of the hair.

The Housing

The device features a housing (1). Normally, the housing is formed of a relatively hard plastic such as ABS (poly-acrylonitrile-butadiene-styrene) which is a high impact resistant plastic.

Preferably, the housing has a gripping portion (7) which can be as simple as an indentation or depression for the thumb. Preferably the gripping portion forms an area that is flush with the housing. In a preferred embodiment, the gripping portion is formed from a material having a relatively high coefficient of friction (relative to that of the housing), which is soft but durable. Such materials can be natural, for example rubber, or synthetic, for example PVC, polyurethane and silicone based materials.

The High Magnification Optic

The high magnification optic is used for obtaining magnified images of surface characteristics of individual hair fibres. For example, details of cuticles and split ends.

The high magnification optic (2) comprises a first lens (9) and a first light source (10). The light source and lens are aligned such that the light source is directed onto the hair and a magnified image of the hair is created through the lens.

The high magnification optic has a slot (4) for locating hair fibres in frame, and a fixed focal length configured such that the located hair fibres are in focus and no manual focusing is required. The slot preferably has a width of from 0.5 to 1.0 mm, more preferably from 0.7 to 0.9 mm, and a depth of from 10 to 20 mm, preferably from 12 to 15 mm.

The resolution of the high magnification optic is preferably in the range of 500 to 1500 times (500 to 1500×), more preferably from 600 to 1000×, most preferably from 700 to 900×.

The number of hair fibres is preferably from 1 to 100, more preferably from 5 to 50. It was found that the number of fibres affected the image quality. We have found that the use of a bundle of 1 to 100, particularly 5 to 50 hairs is particularly advantageous in the attainment of at least one hair in focus at any one time. Thus no manual focusing is required to obtain a focused image.

The high magnification optic is advantageously used to obtain high quality images of the hair fibres along the length of the shaft and the tips of the fibre when the hair is attached to the head of a user. It can also be used to image the roots, when using loose hairs.

The Low Maginification Optic

The low magnification optic comprises a second lens (11) and a second light source (12). The light source and lens are aligned such that the light source is directed onto the hair and/or scalp and a magnified image of the hair and/or scalp is created through the lens. The low magnification optic (3) is preferably located at the tip of the hand held imaging device that can be held in close proximity to the scalp and hair.

The resolution of the low magnification optic is preferably in the range of 10 to 200 times (10 to 200×), more preferably from 25 to 150×, most preferably from 30 to 100×.

The low magnification optic may have a fixed focal length or a variable adjustable focal length.

Where the focal length is fixed, the low magnification optic preferably has a spacer cap (8), to give the correct spacing between the lens and the surface.

Where the focal length is variable, a focusing means is required. This may adjust the position of the lens or the length of the microscope. A preferred focal means is a focusing wheel. An adjustable focusing cap may be adjusted by pulling or twisting the cap to alter the length, thus changing the focus.

The low magnification optic comprises a second light source.

The second light source preferably comprises more than one light, preferably from four to ten lights, most preferably eight lights, spatially arranged (14) around the low magnification optic, located at the tip of the device. Preferably, this is achieved by positioning the lights on a ring (15) supporting the lights. Preferably, the lights are Light Emitting Diodes (LEDs).

The low magnification optic preferably has a light polarisation assembly, such that polarised and non-polarised illumination can be selected. Preferably, the light polarisation assembly is powered and/or controlled remotely from a software application. Alternatively, the polarization can be controlled by mechanical means, preferably with a button or by twisting a cap, such as a spacer cap, at the low magnification end of the microscope. Polarisation can enable better images of features of the hair and scalp to be obtained.

The low magnification optic is used for obtaining magnified images of the scalp and hair. The low magnification optic is advantageously used to obtain high quality images of the hair root area (near the scalp) and of the scalp when the hair is attached to the head of a user. It may be used to obtain images of all parts of the fibre when using loose hairs. The low magnification optic highlights a number of features which can be indicative of attributes linked with healthy or damaged hair, for example scalp sebum; scalp dandruff; hair abundance (how many hairs in a specific area of scalp) and follicle occupancy (number of hairs coming out of each follicle.

The Viewing Means

Preferably, supporting software captures the data signal from the microscope and converts it to a digital image, which can then be shown on the viewing means.

The device comprises a viewing means, which is selected from an integral viewing means, an external viewing means and a combination thereof.

The viewing means is for the purpose of viewing images of the hair and scalp that are obtained by the high magnification optic and the low magnification optic of the device.

The images may be viewed directly through a viewing means that is internal to the device, such as a small screen built into the device. The images may be transferred to an external viewing means such as a screen.

Suitable integral viewing means include a screen that is integral to the housing of the device, and an integral eye piece. Such a screen will be a miniature screen, compatible with the size of the hand held imaging device.

Preferably, the viewing means is an external viewing means. Where an external viewing means is used, means for connecting to an external viewing means will be required. Preferred means for connecting are a USB connector, a phono connector and wireless connectivity.

Preferably the external viewing means is a separate device, that comprises a screen, to which the hand held imaging device of the present disclosure can be releasably connected. Preferred such separate devices include a computer, a monitor, a mobile phone, a tablet and a laptop.

Image Capture

The hand held device may comprise an optional shutter operating means, for example a shutter button (6). It is preferred if the shutter operating means is located on the opposite side of the housing to the slot. This promotes ease of operation with one hand whilst the device is in use.

The images of the hair and scalp can be displayed on a screen. Images may be captured (for example recorded or saved) on a software device.

The images are used to make an assessment of the condition of the hair and/or scalp. The images may also be used in conjunction with the output from an algorithm to evaluate hair or scalp condition.

An assessment may be made by comparison to a set of images showing incremental differences in a condition of the hair, such as damage. Damage may be shown, for example, by cuticle lifting, cuticle erosion, split ends and so on. This will be apparent from images obtained from the high magnification optic.

Similarly the features can be assessed which will be apparent from images obtained from the low magnification optic, which can be indicative of a number of attributes linked with healthy or damaged hair, for example scalp sebum; scalp dandruff; hair abundance (how many hairs in a specific area of scalp) and follicle occupancy (number of hairs coming out of each follicle.

A product recommendation may be made by comparing the assessment to a list of products designed to alleviate the conditions of the hair, such as cuticle lifting, cuticle erosion, split ends, presence of sebum, dandruff, hair abundance, follicle occupancy and so on. This may be carried out manually or by software or algorithm means. An algorithm may provide a method for recommending hair-care products according to how relevant they are for individual consumers, based on benefits claimed on the products.

Connectivity

The imaging device of the present disclosure preferably comprises a means for connecting to a software device, preferably selected from a USB connector, Bluetooth connectivity, wireless connectivity and serial port connection routes.

The imaging device may be connected to a software device. Preferably the software device is selected from a computer, a mobile phone, a tablet and a laptop computer. Connection to a software device enables images of hair to be transferred to the software device. The images may then be displayed for viewing.

Preferably, power to the system is delivered externally from an electric grid. More preferably, power is delivered from a device, preferable a software device to which the hand held imaging device of the present disclosure may be releasably connected. Alternatively, power can be supplied by a rechargeable battery or disposable batteries within the device.

Most preferably the means for connecting the hand held imaging device to a software device, the external viewing means and the power delivery are all facilitated through a single connection.

The Workstation

The workstation comprises the hand held imaging device and a screen, preferably a software device, wherein the hand held device and the screen are positioned on a unitary base. The workstation may further comprise a holder for the hand held imaging device.

The screen is preferably selected from a computer, a monitor, a mobile phone, a tablet and a laptop, most preferably a software device selected from a computer, a mobile phone, a tablet and a laptop. Preferably, the screen can be used separately or in conjunction with the microscope.

The base preferably includes cable storage. Preferably, the power inputs for the hand held imaging device and the screen are integrated into the unitary base, such that it is only necessary to connect the base to a power source in order to power all of the components.

The components of the workstation, for example the hand held imaging device, the screen, the optional holder and the base, are preferably encased in the same material as the housing (1) of the hand held imaging device. Thus the components of the workstation have a unified look and colour. The gripping area material may also be replicated on the base and/or screen casing.

The Method

A method for evaluating condition of hair and scalp using the imaging device of the present disclosure, and of recommending products appropriate to the condition of the hair comprises the steps of:—

1) placing hair fibres (13) in the slot (4) and obtaining a high resolution image of the fibres; 2) placing the low magnification optic (3) onto the hair or scalp and obtaining an image; 3) using the images of steps 1) and 2) to make an assessment of the condition of the hair and/or scalp; and 4) using the assessment of step 3) to provide a product recommendation.

The above method may be carried out on hair that is attached to a participant's head, or on loose (detached) hair. Where the method is carried out on hair that is attached to a participant's head, step 1) is preferably carried out on the shaft and tips of the hair fibres, and step 2) is preferably carried out at the root end of the hair.

The hand held imaging device of the present disclosure is particularly useful in assessing the following aspects of hair and scalp condition. Hair alignment, cuticle condition and colour fade can be assessed along the entire length of the hair fibre. Split ends, bobbles and kinks are particularly relevant to assessment at the tip end of the hair fibre. Indicators of scalp condition such as flakes, dryness and greasiness are advantageously evaluated using the hand held imaging device of the present disclosure, as are fibre density (i.e. the number of fibres per unit area) and multiple occupancy (the number of fibres per follicle).

The number of hair fibres used in the above methods is preferably from 1 to 100, more preferably from 5 to 50.

A participant may monitor their hair and scalp over a period of time. A product recommended to adjust the participant's hair and/or scalp into an improved condition may be applied over the monitored period. The method given above may be repeated. This allows a consumer to evaluate effectiveness of the product or any other products that might be applied to improve the hair and/or skin (scalp) condition.

The invention claimed is:

1. A hand held imaging device for measuring characteristics of hair and scalp, comprising a housing with a high magnification optic for obtaining magnified images of surface characteristics of hair fibres, said high magnification optic comprising a first lens and a first light source, and a low magnification optic, said low magnification optic for obtaining magnified images of the scalp and hair independent of said high magnification optic and comprising a second lens and a second light source, wherein the high magnification optic has a fixed focal length and a slot for locating hair fibres in frame such that the hair fibres are in focus and wherein the device further comprises a viewing means, selected from an integral viewing means, an external viewing means and a combination thereof.

2. An imaging device as claimed in claim 1, wherein the low magnification optic has a light polarisation assembly, such that polarised and non-polarised illumination can be selected.

3. An imaging device as claimed in claim 2, wherein the light polarisation assembly is powered or controlled remotely from a software application.

4. An imaging device as claimed in claim 1, wherein the low magnification optic has a fixed focal length.

5. An imaging device as claimed in claim 4, wherein the low magnification optic has a cap, to give the correct spacing between the lens and the surface.

6. An imaging device as claimed in claim 1, wherein the slot has a width of from 0.5 to 1.0 mm and a depth of from 10 to 20 mm.

7. An imaging device as claimed in claim 1, wherein from 1 to 100 hair fibres are held in the slot.

8. An imaging device as claimed in claim 1, wherein the low magnification optic has a resolution in the range of 10 to 200 times (10 to 200×) and the high magnification optic has a resolution in the range of 500 to 1500 times (500 to 1500×).

9. An imaging device as claimed in claim 1, which comprises more than one light spatially arranged circularly around the low magnification optic located at a tip of the device.

10. An imaging device as claimed in claim 1, further comprising a software connection mechanism configured to connect to a software device.

11. An imaging device as claimed in claim 10, which is connected to a software device.

12. An imaging device according to claim 11 in which images are transferred to the software device.

13. An imaging device as claimed in claim 12, wherein the software device has an algorithm that provides a method for recommending hair-care products according to how relevant they are for individual consumers, based on benefits claimed on the products.

14. A method for evaluating condition of hair and scalp using the imaging device of claim 1, and recommending products appropriate to the condition of the hair, which method comprises the steps of:
  1) placing hair fibres in the slot and obtaining a high resolution image of the fibres;
  2) optionally placing the low magnification optic onto the hair or scalp and obtaining an image;
  3) using the images of steps 1) and 2) to make an assessment of the condition of the hair or scalp; and
  4) using the assessment of step 3) to provide a product recommendation.

15. A workstation comprising the hand held imaging device of claim 1, and a screen, wherein the hand held device and the screen a positioned on a unitary base.

* * * * *